United States Patent [19]
Connor

[11] Patent Number: 6,080,143
[45] Date of Patent: Jun. 27, 2000

[54] INTRAOCULAR SLIT ILLUMINATOR AND METHOD THEREFOR

[76] Inventor: Christopher Sheldon Connor, 37 Carriage La., Hanover, N.H. 03755

[21] Appl. No.: 08/777,066

[22] Filed: Dec. 30, 1996

Related U.S. Application Data

[62] Division of application No. 08/358,946, Dec. 19, 1994.

[51] Int. Cl.[7] ............................................... A61B 17/36
[52] U.S. Cl. .................................................. 606/4; 606/17
[58] Field of Search ................... 606/4, 5, 6, 10, 606/11, 12, 14, 15, 16, 17

[56] References Cited

U.S. PATENT DOCUMENTS

| | | | |
|---|---|---|---|
| 4,993,412 | 2/1991 | Murphy-Chitorian | 606/7 |
| 5,123,902 | 6/1992 | Müller et al. | 606/4 |
| 5,263,950 | 11/1993 | L'Esperance, Jr. | 606/4 |
| 5,282,798 | 2/1994 | Bruse et al. | 606/4 |
| 5,300,063 | 4/1994 | Tano et al. | 606/4 |
| 5,318,560 | 6/1994 | Blount et al. | 606/4 |
| 5,425,730 | 6/1995 | Luloh | 606/4 |
| 5,478,338 | 12/1995 | Reynard | 606/15 |
| 5,558,669 | 9/1996 | Reynard | 606/15 |
| 5,578,007 | 11/1996 | Imran | 606/15 X |
| 5,591,160 | 1/1997 | Reynard | 606/15 |
| 5,603,710 | 2/1997 | Easley et al. | 606/15 |
| 5,624,438 | 4/1997 | Turner | 606/4 |

*Primary Examiner*—Linda C. M. Dvorak
*Assistant Examiner*—Sonya Harris-Ogugua
*Attorney, Agent, or Firm*—Greenberg Traurig; Richard E. Kurtz

[57] ABSTRACT

An intraocular light probe has a slit-shaped mask or cannula affixed at a distal end thereof which forms a slit-shaped light beam for intraocular slit-illumination of target features within the eye. A hood at a distal tip portion directs light in a particular direction. A distal flange retains the instrument within the eye. In a second embodiment, a light probe for intraocular application of a slit-shaped light beam is created by forming a slit shape at a distal end of an optical fiber bundle. A third embodiment provides a surgical instrument, such as a phacoemulsifier or vitrector, having an infusion sleeve which incorporates a slit illuminator for intraocular application of a slit-shaped light beam to target tissues. The device of the invention is preferably introduced into the eye via the primary or side-port incision to provide intraocular cross-lighting of tissues during surgical procedures such as cataract extraction, vitrectomy, intraocular lens implantation, refractive surgery, and glaucoma surgery.

5 Claims, 3 Drawing Sheets

INTRAOCULAR SLIT ILLUMINATOR AND METHOD THEREFOR

This application is a division, of application Ser. No. 08/358,946, filed Dec. 19, 1994.

BACKGROUND OF THE INVENTION

1. Field of the Invention

The invention relates in general to illuminators for illuminating a field of view, and in particular to a device for intraocular application of a slit-shaped beam to ocular structures for purposes of diagnosis and treatment of ophthalmic conditions.

2. Related Art

The use of an externally-applied slit-shaped light beam has been known in office and surgical settings for illuminating ocular structures, such as the cornea and lens surfaces and intraocular fluids. These structures, which are nearly-transparent, are difficult to distinguish using conventional illumination due to the small amount of light scatter which they produce when diffusely lit. The use of a slit-shaped beam allows selective, directed, and intense illumination of nearly-transparent tissues such that even a relatively small amount of scatter by such tissues allows them to be distinguished and otherwise observed or targeted for surgical modification or removal. The slit-illumination also provides a sense of depth, thickness, and three-dimensions to these transparent structures, especially when applied obliquely.

Fiber optic intraocular light sources are known. Such sources have been incorporated into intraocular scissors and forceps for illuminating the proximity of the distal end of such instruments. However, such devices have not provided the advantages of slit-beam illumination, e.g., selective, directed, and intense illumination of target tissues with high contrast.

U.S. Pat. No. 4,138,191 to Peyman et al. discloses a stereo viewing operating microscope for use in optical microsurgery. The microscope is provided with an external slit-shaped beam source for illumination. The slit-shaped beam source is movable, independent of the viewing optics, on an arcuate track.

U.S. Pat. No. 4,565,197 to Daly discloses an aiming/illumination system for use in conjunction with an invisible beam laser for microsurgery procedures. The invisible beam and an aiming (visible) beam are applied along a common axis which is displaced with respect to that of a slit lamp beam and also is displaced with respect to a line of sight of viewing optics. All three axes converge at a common focus point, providing selective illumination/targeting of an area of interest. The system disclosed is non-invasive, with all three light sources being applied externally to the eye.

The aforementioned prior art devices suffer from the disadvantage that ocular structures (i.e., the cornea) which intervene between the light source and the target tissues cause scattering of the illumination light, thereby increasing glare and reducing contrast of the target tissues with respect to such intervening structures and lowering the intensity and quality of the illumination light reaching the target tissues.

SUMMARY OF THE INVENTION

It is therefore an object of the invention to provide an ocular illumination system which can selectively and intensely illuminate target tissues, with decreased scattering by intervening tissues.

It is a further object of the invention to provide an improved method of illuminating intraocular target tissues.

According to a first embodiment, the invention provides an intraocular light probe having a slit-shaped mask or cannula affixed at a distal end thereof for forming a slit-shaped light beam. The device according to the invention may further comprise a hood at a distal tip portion for directing light in a particular direction, and/or may comprise a distal flange for self-retaining the instrument within the eye. In a further embodiment, a light probe for intraocular application of a slit-shaped light beam is created by forming a slit shape at a distal end of an optical fiber bundle. An alternative embodiment provides a surgical instrument, such as a phacoemulsifier or vitrector, having a fluid-infusion sleeve which incorporates a slit illuminator for intraocular application of a slit-shaped light beam to target tissues. The slit-shaped beam may be incorporated into a fluid-infusion sleeve alone, and used independent of another surgical instrument.

The device of the invention is preferably introduced into the eye via a side-port incision to provide intraocular cross-lighting of tissues during surgical procedures such as cataract extraction, vitrectomy, intraocular lens implantation, refractive surgery, and glaucoma surgery. When incorporated with a surgical instrument, such as a phacoemulsifier or vitrector, the device is preferably introduced into the eye through the primary, and not the side-port, incision.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating principles of the invention.

DETAILED DESCRIPTION OF THE DRAWINGS

Figure 1:
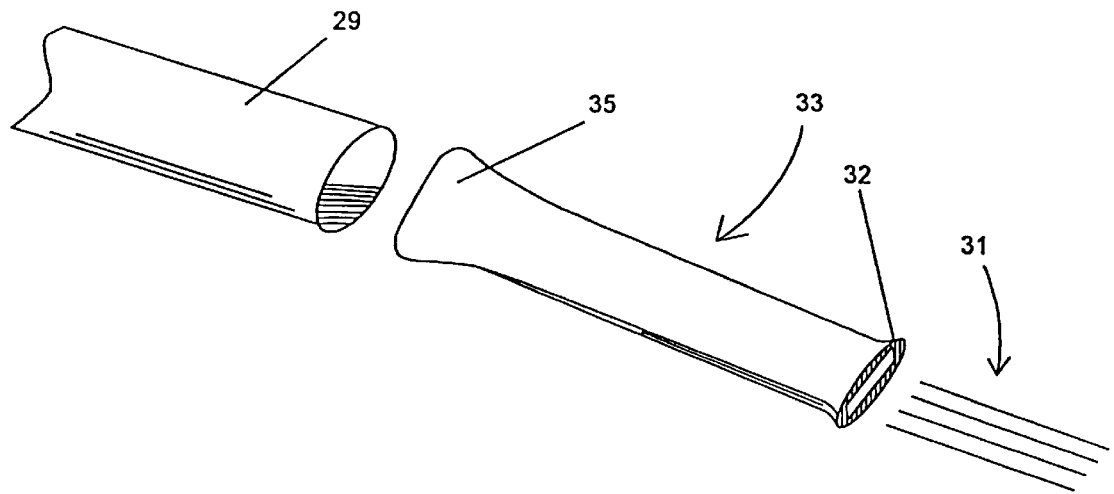
FIG. 1 is an exploded perspective view illustrating a first embodiment of the invention comprising a light probe having a mask thereon for forming a slit-shaped beam.

As illustrated in FIG. 1, a first embodiment of the invention provides an intraocular illuminator comprising a standard light probe 29 having a slit-shaped mask or cannula 33 removably affixed at a distal end thereof for forming a slit-shaped light beam 31. The probe 29 preferably comprises a 19 or 20 gauge rounded light probe. The mask has an opening which emits a slit-shaped beam preferably having an aspect ratio of around 4:1. However, masks of different shapes and sizes may be provided so as to selectively provide an illuminating beam in the form of a slit, rectangle, pinpoint, etc.

The mask 33 is constructed such that its distal tip can be inserted into the eye through a small side-port incision. The height of the emitted beam is preferably within the range of 0.125 mm to 0.5 mm, and the width is preferably within the range of 0.5 mm to 2.0 mm. A flared lip 35 of the mask or cannula 33 receives an end portion of the probe 29 and is preferably affixed thereto via a tight-fitting male-female friction joint. That is, the probe 29 is pressed into the flared lip 35 with sufficient force to cause it to be wedged into the tapered opening of the flared lip 35 such that a secure, removable joint is formed. Alternatively, the joint may be made via a well-known "Luerlok" connection, in which the male feed is inserted into the female flared lip and is then rotated 90 degrees to a locked position. Other known joining means, such as threading on both the feed and the mask, may also be employed without departing from the spirit and scope of the invention.

The device according to the invention may further comprise a flange 32 at a distal end of the mask 33. The flange 32 is useful for self-retaining the distal end of the mask 33 or the probe within the eye.

The mask may be constructed of sterilizable plastic, stainless steel, titanium, or other suitable material. A mask having a sterilizable plastic construction is generally less costly to produce and thereby is more economically feasible for applications where the tip is intended to be disposable after use. On the other hand, a mask having a stainless steel or titanium construction could be made autoclavable and thereby re-usable. The mask 33 can be made integral with the probe when the probe is manufactured. In such an embodiment, there is no requirement that the device comprise a joining means (such as the flared lip 35 or Luerlok, discussed above) for joining the mask 33 with the probe 29. As shown in FIG. 1, masking is done at the distal end of the mask or cannula 33; however, it is noted that such masking can alternatively be done at the proximal end.

Figure 2:
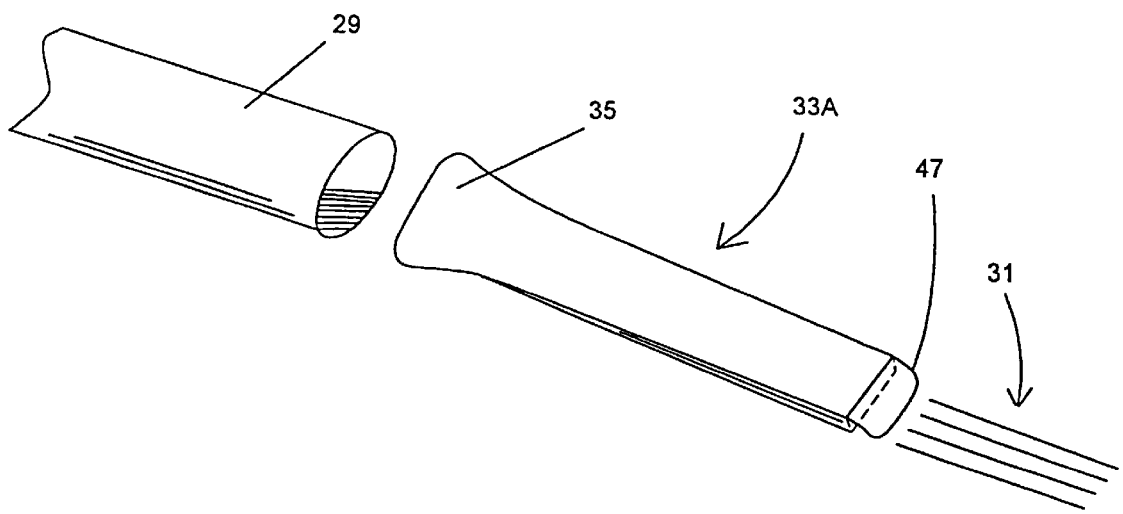
FIG. 2 is an exploded perspective view illustrating an embodiment of the invention as in FIG. 1 but having a distal hood.

As illustrated in FIG. 2, the device according to the invention may comprise a hood 47 at a distal end of the mask 33a. The hood 47 is useful for diverting light to a desired direction and for lessening light dispersion. It should be understood that a single intraocular slit-illuminator of the invention may comprise both the hood 47 and the flange 32 (FIG. 1), either as separate elements or as a single element performing both as a flange and a hood.

Figure 3:
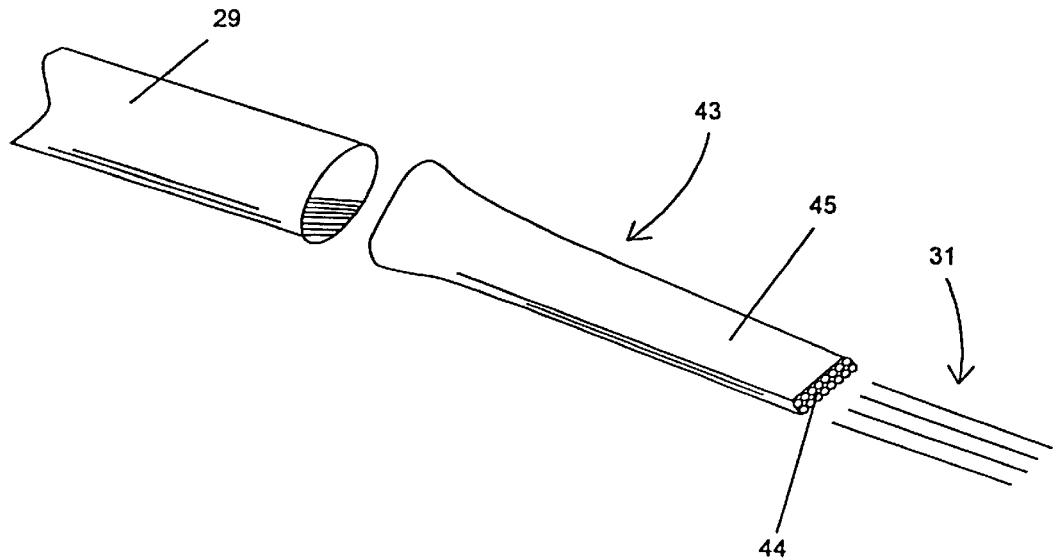
FIG. 3 is an exploded perspective view illustrating a further embodiment of the invention comprising a light probe having affixed thereto a bundle of optical fibers formed to shape light transmitted therethrough into a slit-shaped beam.

FIG. 3 illustrates the invention according to an alternate embodiment, wherein a light probe for intraocular application of a slit-shaped light beam 31 is created by forming a slit shape at a distal end of an optical fiber bundle 44. The slit-shaped bundle 44 may be encased in a sleeve 45 which is attached to a light probe 29 in much the same manner as that which is discussed above with respect to the first embodiment of the invention.

Figure 4:
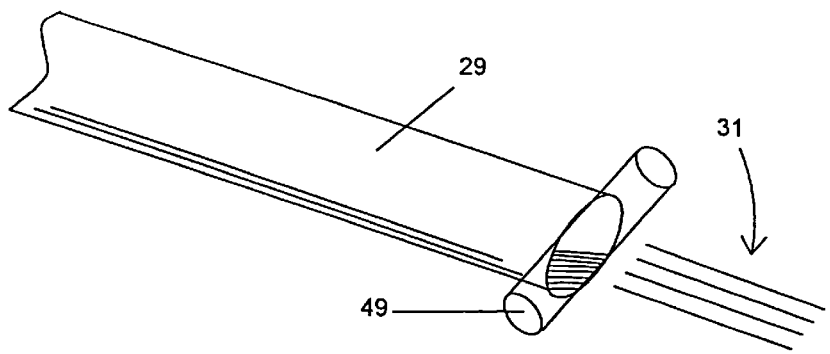
FIG. 4 is a perspective view illustrating a fourth embodiment of the invention wherein a cylindrical focusing lens is used to form a slit-shaped beam.

FIG. 4 illustrates an embodiment of the invention in which the function of forming a beam emitted by probe 29 into a slit-shaped beam 31 is performed by a cylindrical focusing lens 49 operatively connected to the probe 29.

Figure 5:
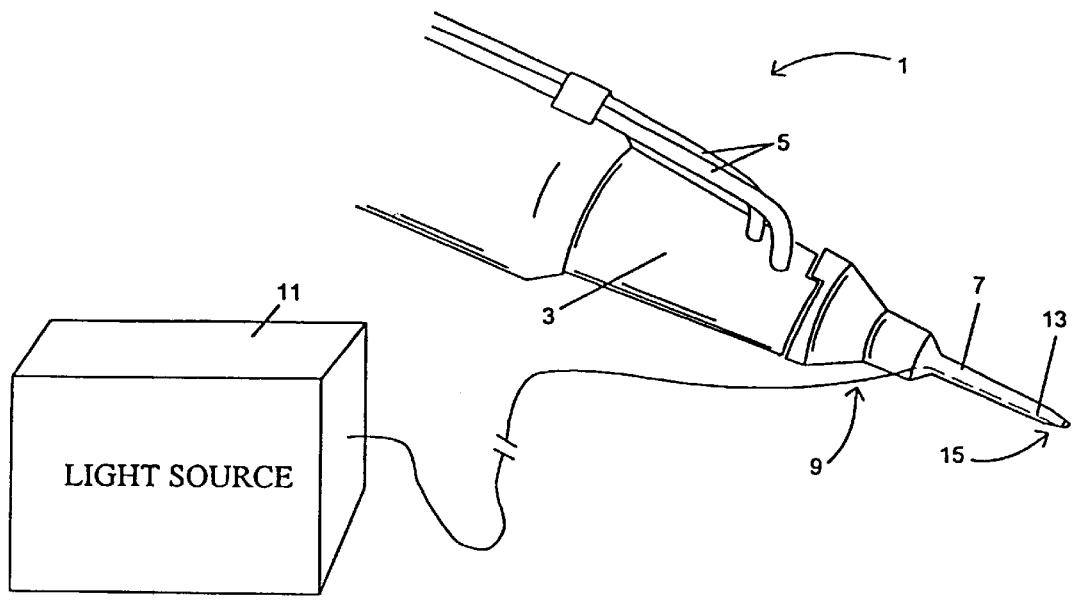
FIG. 5 is a perspective view illustrating a fifth embodiment of the invention wherein a slit illuminator is incorporated into an infusion sleeve of a surgical instrument.

Referring to FIG. 5, an intraocular slit illumination system 1 includes a modified surgical instrument 3, which may be a phacoemulsifier, a vitrector, an irrigator/aspirator, or other intraocular instrument. A distal end 15 is introduced into the eye. Irrigation and aspiration tubes 5 provide irrigation and aspiration to the distal end 15. The surgical instrument 1 is provided with an infusion sleeve 7 which incorporates a slit-illuminator 13 for intraocular application of a slit-shaped light beam to target tissues within the eye. A light source 11 supplies light to the slit illuminator 13 via a feed 9.

Figure 6:
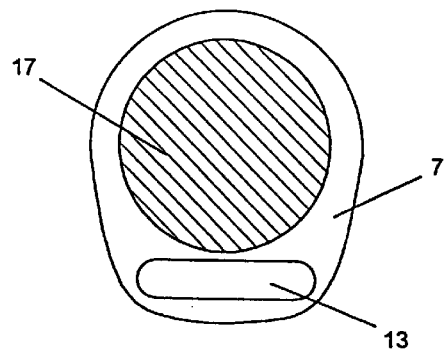
FIG. 6 is a cross-sectional view of a slit-illuminator sleeve according to the invention.

Referring to FIG. 6, the slit illuminator 13 preferably comprises a slit-shaped channel incorporated into a sleeve 7. The sleeve 7 is fitted onto the tip 17 of a surgical instrument. The tip 17 may comprise, e.g., a phacoemulsification tip, a vitrectomy tip, an irrigator/aspirator, or the like. Alternatively, the sleeve may be used independently of a surgical instrument. As will be appreciated by those skilled in the art, the sleeve 7 for intraocular illumination may include a channel having a shape other than a slit-shape, i.e., it may have an oval or rounded profile, without departing from the spirit and scope of the invention. Such a device is useful for providing an instrument with the capability of intraocular illumination without adding significant bulk over an identical instrument not having an illumination means thereon.

The device of the invention is preferably of a construction which is autoclavable, retains sterility well, can be immersed in fluids, and which does not generate excessive heat. The infusion sleeve embodiment can be constructed of disposable plastic, silicone or other suitable material. It can alternatively be constructed of an autoclavable material such as stainless steel.

Further, it is advantageous to provide the slit illuminator of the invention with adjustable brightness control, such as by using a light source 11 (FIG. 1) having variable intensity.

The device of the invention is useful providing illumination of target tissues during surgical procedures such as cataract extraction, vitrectomy, intraocular lens implantation, refractive surgery, and glaucoma surgery. Generally, a small side-incision, preferably 1–2 mm in length, is made in the outer periphery of the cornea (the limbus) and the slit illuminator is introduced through the incision to provide cross lighting of target tissues with respect to the line-of-sight of an ocular microscope. When combined with another surgical instrument, such as a phacoemulsifier or vitrector, the device enters the eye through the primary incision, whether that incision is at the cornea, limbus, or sclera. The site of entry can be even further posterior along the sclera, to illuminate more posterior intraocular structures such as the vitreous and the retina. Further, an intraocular slit illuminator may be used in combination with a laser to improve target illumination, aiming and focusing of the laser during microsurgery.

While the invention has been particularly shown and described with reference to a preferred embodiment thereof, it will be understood by those skilled in the art that various changes in form and details may be made therein without departing from the spirit and scope of the invention.

The embodiments of the invention in which an exclusive property or privilege is claimed are defined as follows:

1. An intraocular surgical instrument for providing illumination of intraocular target structures within an eye during surgical procedures for diagnosis or treatment of ocular conditions, comprising:

a distal tip portion capable of insertion into the eye;

a sleeve fitted to said distal tip portion, said sleeve further comprising:

a channel having an illumination means therein, said illumination means emitting a light beam for intraocular application of illumination light to target structures within the eye.

2. The device according to claim 1, wherein said illumination means comprises a slit-beam illuminator.

3. The device of claim 1, wherein said sleeve comprises an infusion sleeve.

4. A method of illuminating intraocular target structures within an eye during surgical procedures for diagnosis or treatment of ocular conditions, said method comprising the steps of:

creating a side-port incision in an outer periphery of said eye;

inserting an illumination means through said side-port incision so as to provide intraocular cross-lighting of target structures within said eye.

5. The method of claim 4, wherein said inserting step comprises the step of inserting through said side port a means for providing slit-illumination, whereby intraocular slit-beam cross-lighting of target structures is achieved.

* * * * *